United States Patent [19]
Baden et al.

[11] Patent Number: 5,735,849
[45] Date of Patent: Apr. 7, 1998

[54] ENDOSCOPIC FORCEPS WITH THUMB-SLIDE LOCK RELEASE MECHANISM

[75] Inventors: Michael Baden, Rogers; Brent Anderson, Delano, both of Minn.

[73] Assignee: Everest Medical Corporation, Minneapolis, Minn.

[21] Appl. No.: 744,409

[22] Filed: Nov. 7, 1996

[51] Int. Cl.$^6$ ..................................................... A61B 17/39
[52] U.S. Cl. ..................... 606/51; 606/52; 606/205; 606/206
[58] Field of Search .................. 606/41, 42, 45–52, 606/205–207

[56] References Cited

U.S. PATENT DOCUMENTS

| | | | |
|---|---|---|---|
| 5,417,203 | 5/1995 | Tovey et al. | 606/205 |
| 5,425,743 | 6/1995 | Nicholas | 606/208 |
| 5,445,638 | 8/1995 | Rydell et al. | 606/51 |
| 5,458,598 | 10/1995 | Feinberg et al. | 606/52 |
| 5,483,952 | 1/1996 | Aranyi | 606/205 |
| 5,499,998 | 3/1996 | Meade | 606/207 |

*Primary Examiner*—Michael Peffley
*Attorney, Agent, or Firm*—Haugen & Nikolai, PA

[57] ABSTRACT

The present invention is a electrosurgical device having an elongated tubular member with a cutting and coagulating arrangement at its distal end and a handle at its proximal end. The coagulating and cutting instrument consists of two electrode jaw members with cutting blade extending therebetween. The cutting blade is connected to a movable rod extending through the lumen of the tubular member. A first and second conductor pair extend through the lumen of the tubular member in a spaced apart parallel arrangement with the cutting instrument and its movable rod extending therebetween. The first and second conductor pairs form the forceps jaws. The forceps jaws have a slot for receiving the cutting instrument therebetween. The handle member affixed to the proximal end of the tubular member includes a selector switch used for selecting a mode of movement of the jaws so that either unidirectional mode or a bidirectional mode can be selected. The device further includes a release connected to the selector means for restoring bidirectional movement of the jaw mechanism if the unidirectional mode had earlier been selected.

12 Claims, 6 Drawing Sheets

ENDOSCOPIC FORCEPS WITH THUMB-SLIDE LOCK RELEASE MECHANISM

I. FIELD OF THE INVENTION

The present invention relates generally to electrosurgical instruments, and more particularly to a bipolar electrosurgical device for coagulation and cutting of target tissue and specifically designed for use in the performance of percutaneous laparoscopic surgery or other endoscopic procedures.

II. BACKGROUND OF THE INVENTION

For a number of years, the medical device industry, in cooperation with health care providers, has been developing methods and devices to permit surgical procedures to be performed in a less invasive manner. Minimally invasive surgery generally involves the use of instruments which avoid the need to make major incisions in the body. Major incisions usually require a relatively long period of hospitalization and subsequent home recovery. Minimally invasive surgery has the salutary effects of shortening hospitalization and recovery times.

Minimally invasive surgery procedures can be performed routinely through a trocar cannula. The cutting and coagulating instruments most often used are either electrosurgical or laser based. While laser based instruments are capable of more precise cutting than electrosurgical instruments, they are somewhat difficult to control, particularly in the close conditions of laparoscopic procedures. Electrosurgical instruments are either monopolar or bipolar in nature. In monopolar electrosurgery, there is a greater potential for injury to body tissues because an electric current must pass through the tissues or a path of least resistance basis to a return electrode located on the patient's skin. In laparoscopic procedures, there is even a greater potential for complications when using monopolar instruments, due to the combined effects of the surgeons limited field of vision, the proximity of other organs to the tissue being cut and the inherent tendency of monopolar RF energy to find a somewhat random path back to the return electrode.

Bipolar electrosurgical instruments provide an improved margin of patient safety in certain minimally invasive surgical and interventional procedures. In bipolar devices, the RF energy is contained at the surgical site because both the active and return electrodes are located in close proximity on the surgical instrument itself.

Bipolar coagulating and cutting forceps with articulable jaws are known, such as U.S. Pat. No. 5,445,638 to Rydell et al. The jaws are used for grasping or gripping the tissue to be cut. The surgeon is limited if a constant force must be maintained on the forcep handles to keep the jaw closed in the desired position. While it has been known to provide jaw locking mechanisms on the handles of surgical instruments, difficulties arise when the jaws are locked in an undesirable position. The surgeon must release the locking mechanism, which in turn, releases the tissue. The surgeon essentially must start all over with grasping the tissue, closing the forceps to the desired position and locking the mechanism.

Consequently, a need exists for an electrosurgical instrument which allows the surgeon to select between a unidirectional feature in which the instrument can be incrementally advanced in one direction, such as closing onto tissue, or bidirectional feature which allows bilateral movement of the cutting and coagulating jaws. A further need exists for such a device to additionally have a temporary release to allow bidirectional movement when the unidirectional feature has been selected.

A SUMMARY OF THE INVENTION

The present invention resides in an electrosurgical device, e.g. a forceps, which allows the operator to choose between a bidirectional mode or unidirectional mode of jaw movement. The device has an elongated tubular member with a proximal end and a distal end. The cutting and coagulating jaw arrangement is located at the distal end of the elongated tubular member. The jaw arrangement includes a first electrode on a first jaw and a second electrode on a second jaw. An arcuate wire means extends proximal from an inner tubular member disposed within the outer tubular member. A moveable guide sleeve is located at the end of the inner tubular member. When the inner tubular member is made to move longitudinally, the guide sleeve selectively engages and deforms the arcuate wire means which in turn opens or closes the jaws. RF voltage is applied across the first and second electrodes for coagulating tissue contained between said first and second jaw.

A handle is located on the proximal end of the elongated tubular member. The handle include two levers. One lever is used to actuate the opening and closing of the jaw arrangement by moving the inner tubular member. The other lever is used for advancing a cutting instrument, such as a scalpel blade, out of the elongated tubular member for cutting through tissue contained between said jaws.

The handle also includes a selector means for selecting either the unidirectional mode or the bidirectional mode for operating the jaws. A thumb slide is located on the handle and has a first position for selecting the unidirectional mode and a second position for selecting the bidirectional mode. In the first position, the slide contacts and tilts a locking washer contained within the handle. The locking washer has a central aperture through which the inner tubular member extends. When the locking washer is tilted at an angle to the inner tubular member, it frictionally engages the inner tubular member. Consequently, the inner tubular member can only move in the forward or distal direction when the jaw actuating lever is depressed, the direction being that needed for closing the jaws. When the actuating lever is released, the inner tubular member stops in its current position and cannot move in one direction because of the frictional force existing between the tipped washer and the inner tubular member. In the slide's second position, it does not engage the edge of the lock washer defining its central aperture. Thus, the inner tubular member can freely move back and forth in either direction.

The handle also includes a trigger for actuating a release means allowing bidirectional movement of the jaws when the unidirectional mode had been selected. This trigger engages the locking washer and moves into a perpendicular position where its edge defining its central aperture does not engage the inner tubular member. The inner tubular member can then freely move back and forth.

The principal object of the present invention is to provide a bipolar electrosurgical cutting and coagulating instrument which has bidirectional and unidirectional modes for actuating the forceps jaws.

Another object of the present invention is to provide a bipolar electrosurgical cutting and coagulating instrument having an unidirectional mode which permits the operator to incrementally close the forceps on the tissue to be coagulated and cut.

Still another object of the present invention is to provide a bipolar electrosurgical cutting and coagulating forceps with a quick-release lever which allows bidirectional movement of the forceps when a unidirectional mode had been chosen.

IV. BRIEF DESCRIPTION OF THE DRAWINGS

The foregoing objects and other features of the invention will become more readily apparent by referring to the following detailed description of the preferred embodiment, taken in conjunction with the accompanying drawings, in which.

DESCRIPTION OF THE PREFERRED EMBODIMENT

Figure 1:
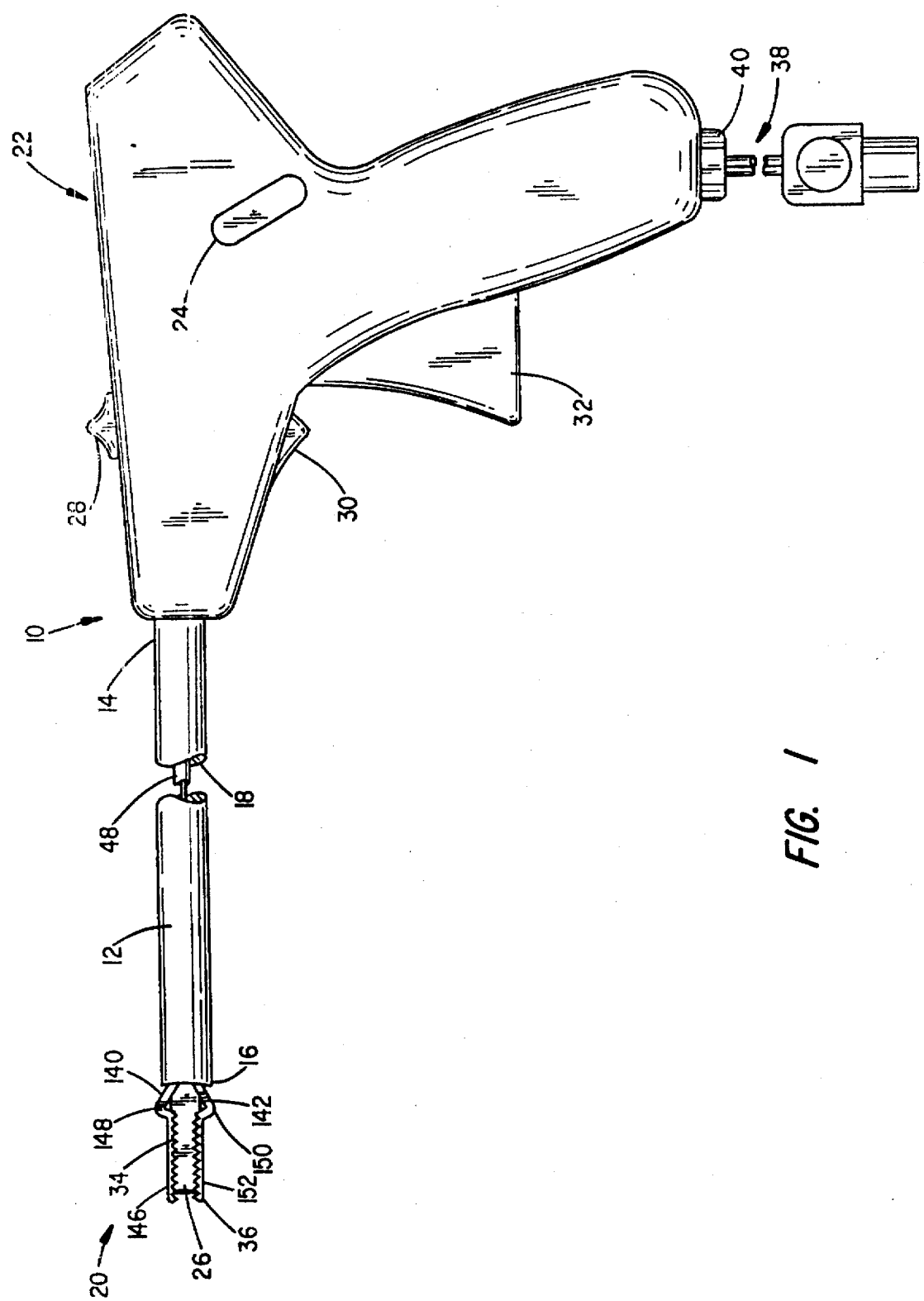
FIG. 1 is a side elevation of a bipolar surgical forceps in accordance with the present invention.

Referring first to FIG. 1, there is indicated generally by number 10, an electrosurgical instrument designed for use in percutaneous laparoscopic surgical procedures. The electrosurgical instrument is a cutting forceps and comprises an elongated tubular barrel member 12 which may be formed from the variety of materials, such as stainless steel. The outer tubular barrel member has a proximal end 14, a distal end 16 and a lumen 18 extending the entire length thereof. The tubular barrel member 12 preferably has an 8 mm lumen and is sized to be used within an trocar with a 10 mm inner diameter.

A cutting and coagulating jaw arrangement 20 extends from distal end 16 and a handle 22 is located at the proximal end 14. The handle 22 includes a spring-loaded thumb lever 24 for actuating cutting blade 26 of the cutting and coagulating jaw arrangement 20. A thumb slide 28 is located on the top of handle 22 for selecting either the bidirectional mode or the unidirectional mode of the cutting and coagulating forceps movement, as will be explained later. A trigger lock release 30, which allows bidirectional movement when the unidirectional mode is selected, is located adjacent a lever 32. Lever 32 is manipulated for actuating the coagulating jaws 34 and 36 of the cutting and coagulating jaw arrangement 20. Insulated electrical leads designated 38 extend from an electrical connector 40 on handle 22 and are adapted to be connected to a source of RF power (not shown).

Figure 2:
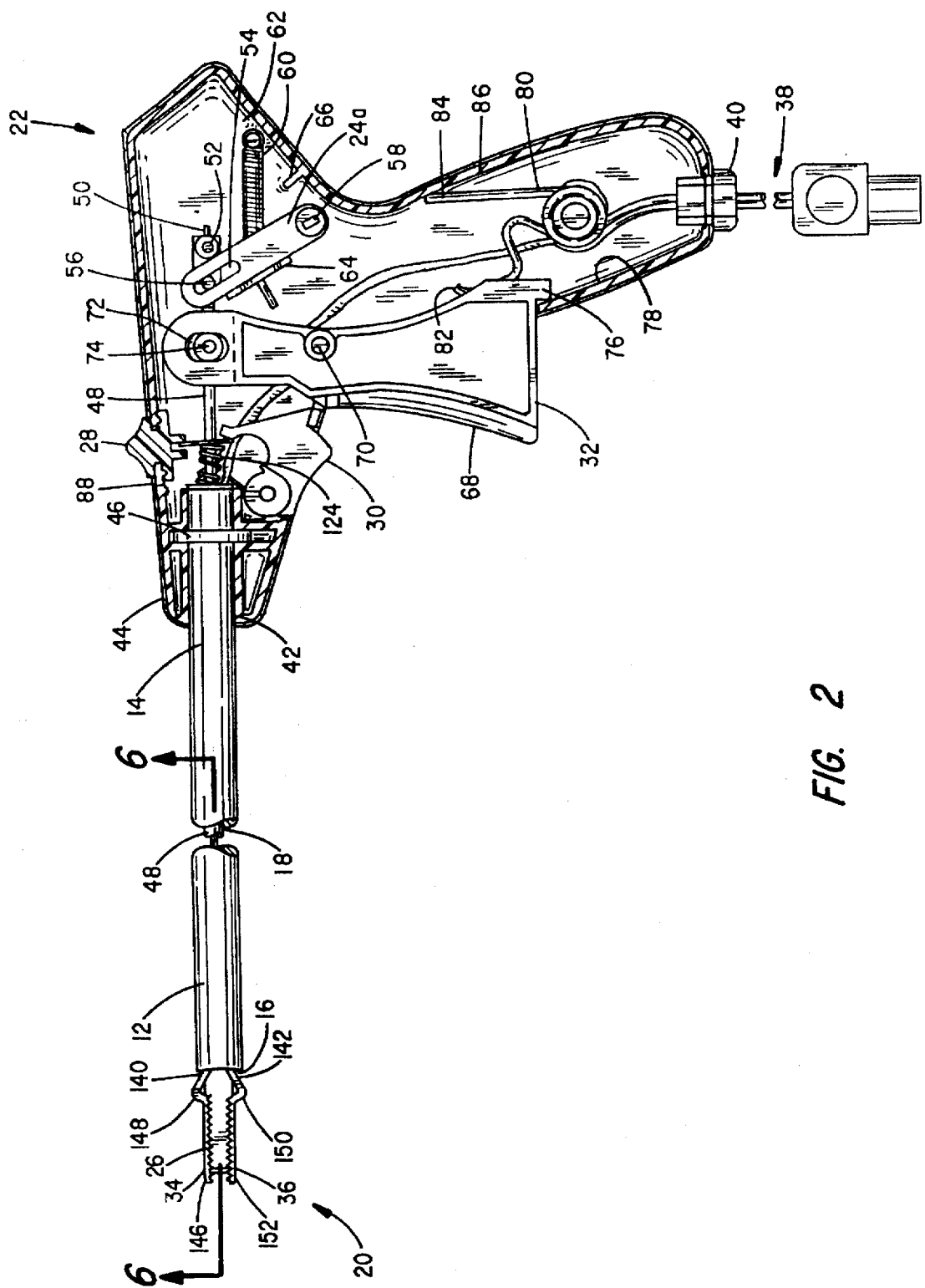
FIG. 2 is a partially sectioned side elevation of a bipolar surgical forceps.

Turning now to FIG. 2, the interior of handle 22 is shown. The proximal end 14 of barrel member 12 extends into a bore 42 formed in the distal end 44 of handle 22. The bore 42 enlarges, forming an annular recess which receives a ring member 46. Ring member 46 is affixed to the barrel member 12 thus securing it to the handle 22.

Projecting out from the proximal end of barrel member 12 into the handle 22 interior is an inner tubular member 48 and a blade rod 50. The blade rod 50 terminates in an clevis arrangement 52. Pivoting blade lever 24 shown in FIG. 1 has an interior lever 24a as seen in FIG. 2. Lever 24a is coupled to blade rod 50 through an elongate slot 54 in which pin 56 is positioned. Lever 24a is pivotally attached to the handle 22 at pivot pin 58. Levers 24 and 24a can be integrally formed or coupled such that they move in unison. A helical tension spring 60 is fixed to a mid-point of lever 24a. Spring 60 is also fixed to a boss formed on the rear interior surface 62 of handle 22. Two stops are formed in the handle cavity for limiting the range of movement of the levers 24 and 24a and in turn the movement of the blade 26. Stop 64 limits forward movement of the levers 24 and 24a, blade rod 50 and blade 26. Stop 66 limits the rearward movement of lever 24a, blade rod 50 and blade 26.

As seen in FIG. 2, an opening is formed in the handle 22 through which the finger engaging portion 68 of trigger or lever 32 extends. Lever 32 is pivotally secured to the handle interior through a pivot pin 70. A slot 72 is located in the upper portion of lever 32. The inner tubular member 48 terminates at a clevis pin arrangement 74 which is coupled to lever 32 through engagement with a slot 72. Lever 32 also includes an extension 76 which extends past the opening and contacts interior surface 78 of handle 22. A torsion spring 80 is located in handle 22 with one end 82 resting against lever 32 and the other end 84 resting against the rear interior surface 86 of handle 22. The torsion spring 80 acts as a biasing means for lever 32 providing a return force to the lever.

Figure 3:
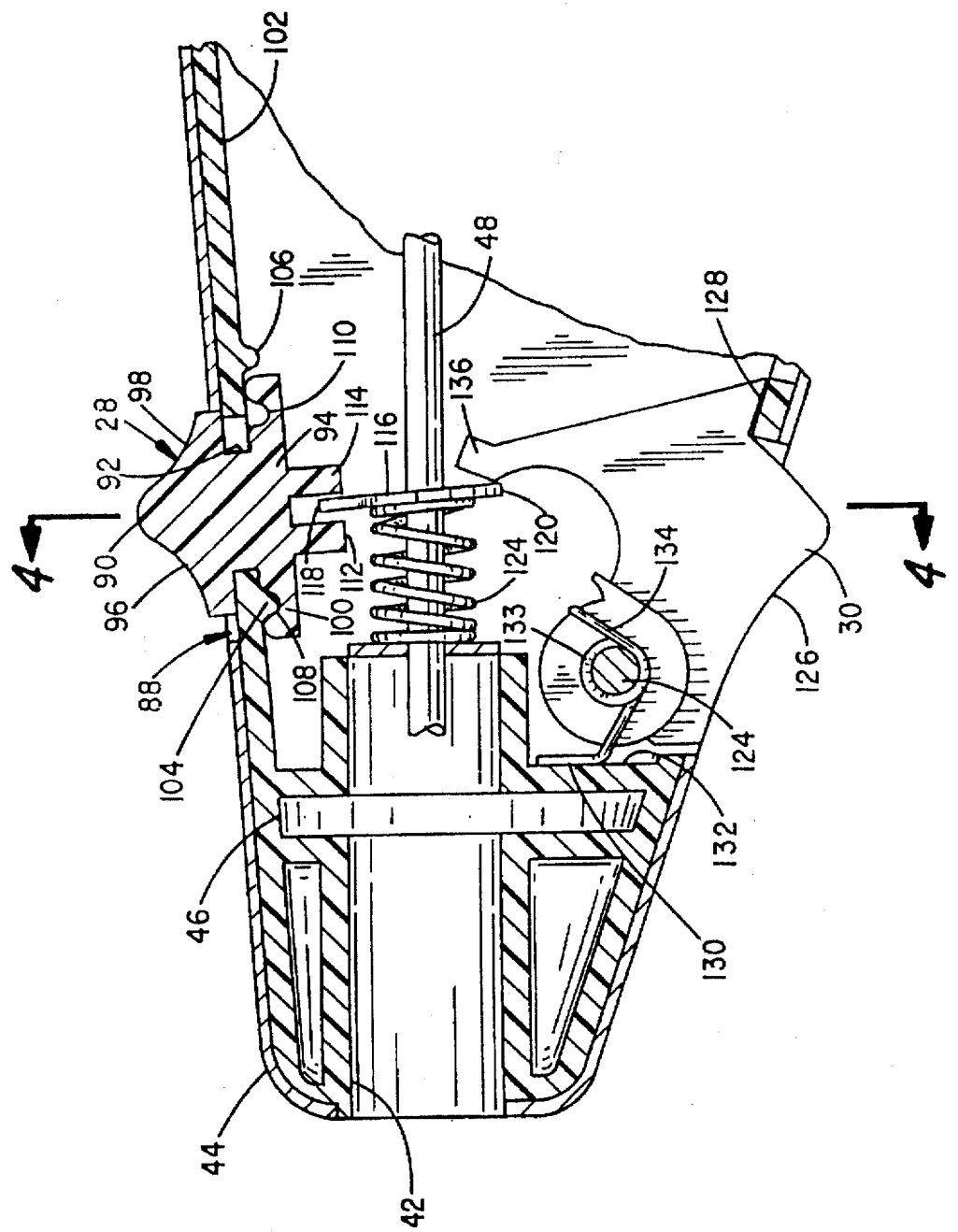
FIG. 3 is an enlarged cross-sectional view of a portion of the handle showing the locking mechanism of the present invention.
Figure 4:
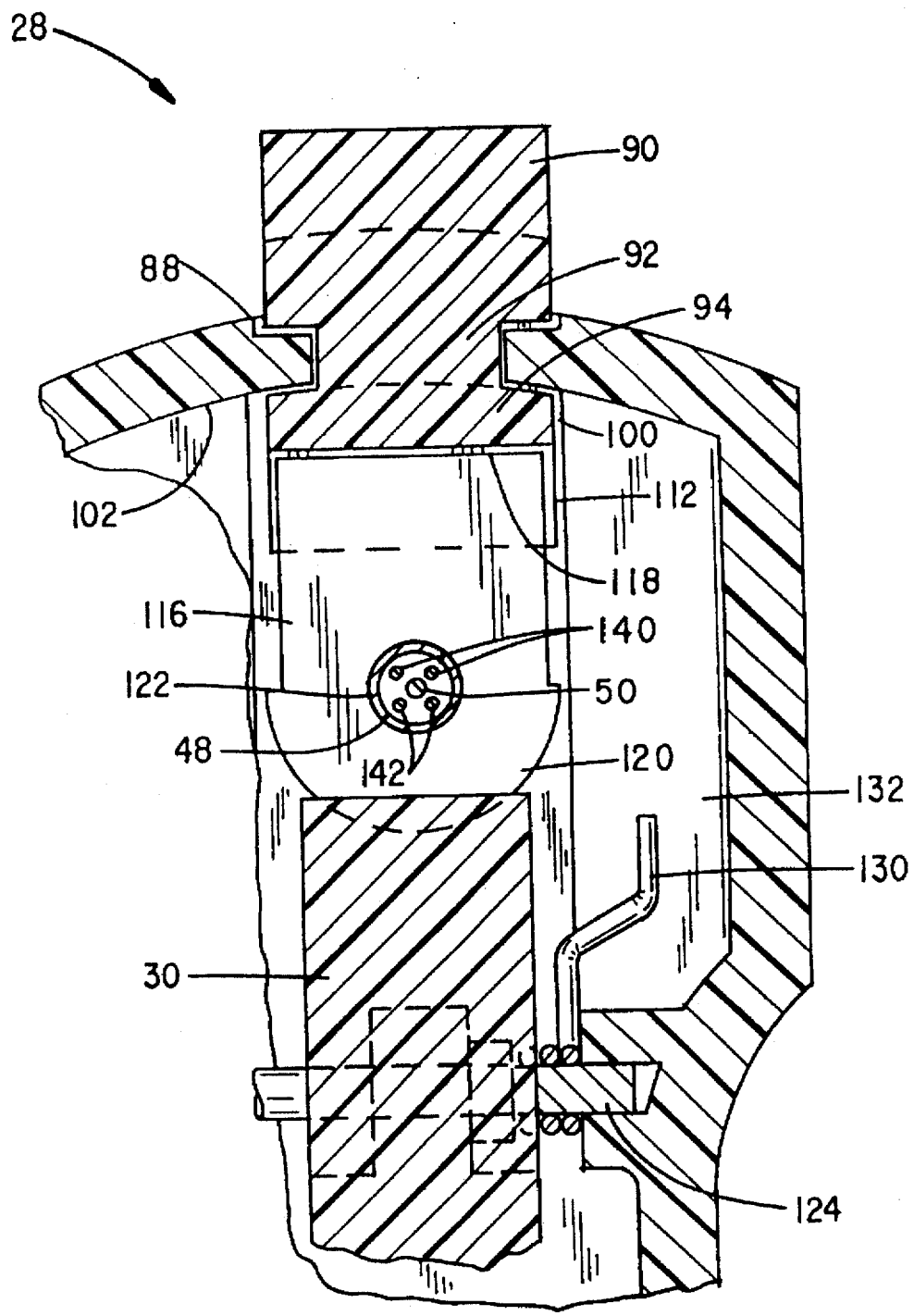
FIG. 4 is a cross-sectional view of the locking mechanism taking along line 4—4 of FIG. 3.
Figure 5:
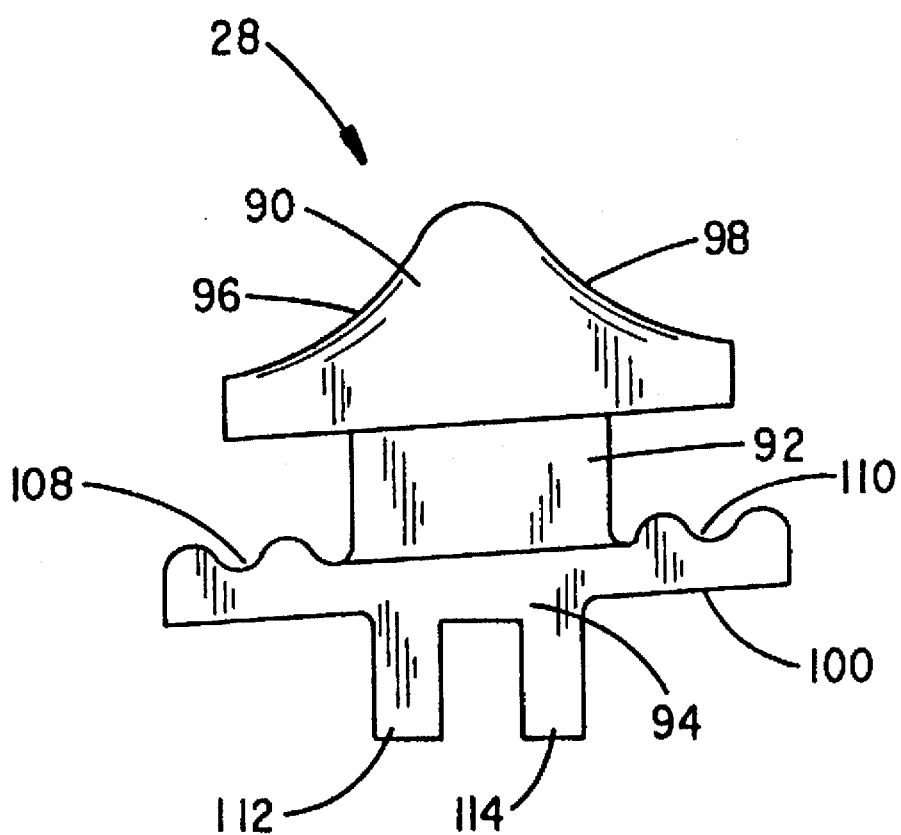
FIG. 5 is a side view of the thumb slide mechanism used in the preferred embodiment of the present invention.

The slide 28 for selecting either the unidirectional mode or bidirectional mode for moving the jaw arrangement, shown in FIGS. 2, 3 and 4, is positioned in a slot 88 formed on the upper portion of handle 22. Slide 28 has an exterior portion 90 (FIG. 3), an intermediate portion 92 and an interior portion 94. The exterior portion 90 has two thumb engaging arcuate surfaces, forward surface 96 and a rearward surface 98. A locking member 100 which is parallel to the upper interior wall 102 of handle 22 is located on the interior portion 94. The interior wall 102 of handle 22 has a rounded detent 104 on a first side of slot 88 and rounded detent 106 on a second side of slot 88. The locking member 100 has detent notch 108 on a first end. Detent notch 108 is configured to receive the detent 104. Likewise, a detent notch 110 is located on a second end of locking member 100. Detent notch 110 is configured to receive detent 106 located on the second side of slot 88. The locking member 100 also includes two spaced apart walls 112 and 114. These wall members receive the edge 118 of locking washer 116 therebetween as seen in FIGS. 2 and 3.

As seen in FIG. 4, the locking washer 116 has a generally rectangular shape with an upper edge 118, a lower arcuate portion 120 and a round aperture 122. The inner tubular member 48 extends through the locking washer with a close tolerance aperture 122. A helical compression spring 124 concentrically surrounds inner tubular member 48 and is positioned between the proximal end 14 of the barrel member 12 and the washer 116 and acts as a biasing means for the locking washer 116.

The locking washer 116 has two positions. In the first position or unlocked position, the locking washer is substantially perpendicular to the inner tubular member 48 as seen in FIG. 4 such that the aperture loosely surrounds the inner tubular member. In the second position or locked position, the locking washer 116 is tipped so that the edge defining the aperture 122 frictionally engages the inner tubular member 48 as seen in FIGS. 2 and 3. The position of washer 116 is determined by the position of thumb slide 28. When thumb slide 28 is in the forward position, detent 104 is received in detent notch 108 and wall 114 engages edge 118. This tips washer 116, arresting rearward, proximal movement of the inner tubular 10 member 48. When the thumb slide 28 is in the rearward position, the detent 106 is received in detent notch 110 and neither wall 112 nor wall 114 engage the washer 116. Spring 124 biases the washer 116 to its upright position such that the edge defining washer aperture 122 does not engage or contact the inner tubular member 48.

The lock release trigger 30 is located below the locking washer 116 within easy reach by a user's forefinger. Trigger 30 is pivotally secured to the handle through pivot pin 124 with a finger engaging portion 126 (FIG. 3) extending out through an opening in handle 22. The trigger 30 includes a stop 128 which extends past the opening on the handle interior and normally rests against interior wall surface 132. A torsion spring 133 is secured at the pivot pin 124. End 130 of the torsion spring 133 rests against the interior wall 132 of handle 22. End 134 of the torsion spring rests against an arcuate surface formed on the trigger 30. An upper surface 136 of trigger 30 contacts the locking washer 116 as seen in FIG. 3.

Figure 6:
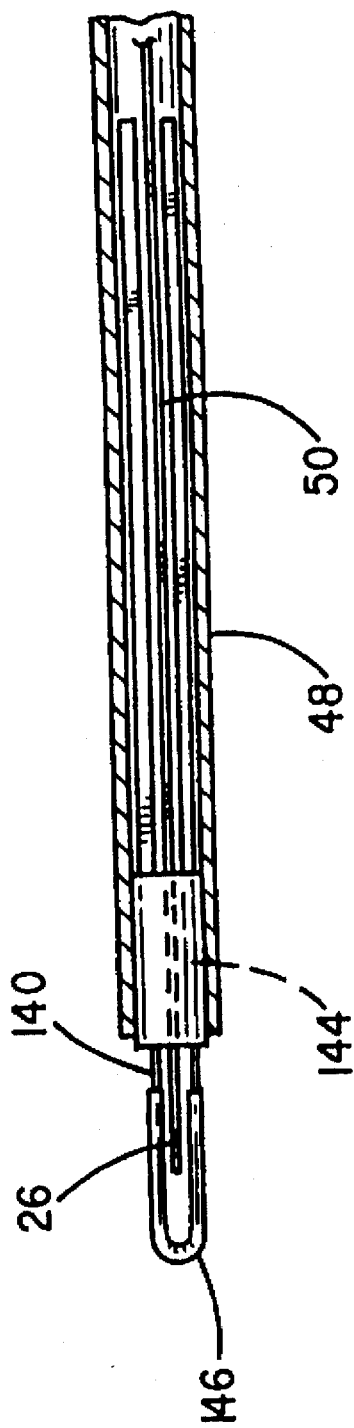
FIG. 6 is a cross-sectioned partial view taken along line 6—6 in FIG. 2 of the present invention.

Turning now to FIGS. 1, 2 and 6, the cutting and coagulating apparatus 20 will now be described. It is substantially the same as is described in the aforereferenced Rydell et al. patent. A first jaw member 34 and a second jaw member 36 perform the grasping and coagulating function of the forceps. The jaws extend from the distal end 16 of the inner tubular member 48 and barrel member 12. Two pairs of conductive wire leads 140 and 142 and the cutting blade rod 50 extend through the entire length of the inner tubular member 48. The leads extend out of the handle 22 and together are identified as insulated electrical leads 38. A conventional scalpel blade 26 or other cutting tool, such as a wire with a sharpened leading and trailing edge, is crimped on the distal end of blade rod 50 and therefore is movable therewith.

A guide sleeve support 144 is press fit in the distal end of the inner tubular member 48 and is shown in hidden line in FIG. 6. The guide sleeve support 144 contains longitudinal bores (not shown) through which the leads 140 and 142 and the blade 26 and associated blade rod 50 extend. The first pair of conductive leads 140 form the first jaw 34 of the coagulating forceps. The wire pair 140 pass through the guide sleeve support 144 and extend from the distal end 16 of the tubular member in spaced apart parallel arrangement, forming a slot for receiving the cutting blade 26 therebetween as shown in FIG. 6. The wires 140 form a generally U-shaped flattened electrode surface 146 at their distal end with an arcuate configuration 148 just proximal of the flattened electrode surface of the first jaw.

The second conductive wire lead pair 142, as seen in FIGS. 2 and 6, forms the second jaw 36 of the coagulating forceps. The second conductive pair 142 extends, like the first pair 140, from the distal end 16 of the tubular member 12 in spaced apart parallel arrangement to each other forming a slot so that the cutting blade 26 can pass freely therebetween. Like the first conductive pair 140, the second pair 142 has an arcuate portion 150 prior to forming a generally U-shaped flat electrode surface 152.

The arcuate configuration of the conductive wire pairs 140 and 142 is necessary to accomplish the closing of the forceps. The guide sleeve support 144 is moved in the distal direction over the arcuate portions 148 and 150 of wires 140 and 142 as the inner tubular member 48 is moved toward the distal end of the forceps. The arcuate portions 148 and 150 are squeezed together, closing the coagulating forceps 32 and 34 against one another or against tissue disposed therebetween. The guide sleeve support 144 is made to move longitudinally inside the outer tubular member and over the leads by effectuating longitudinal displacement of the inner tubular member 48 via the lever 32.

VI. MODE OF OPERATION

The present invention is intended to be used in conjunction with a cannula, however it is not limited to such use. The bipolar endoscopic forceps 10 will have its tubular member 12 inserted through the lumen of a cannula extending into the patient. The surgeon views the surgical site with a laparoscope. The bipolar coagulating forceps jaws 34 and 36 are positioned about the tissue to be cut and coagulated. The surgeon selects either the unidirectional mode or the bidirectional mode for actuating the biopsy jaws.

In the unidirectional mode, the jaws 34 and 36 can only move towards each other to close on the tissue to be grasped, cut and coagulated. If pressure on the lever 32 is released, the jaws 34 and 36 remain in the position they were in when the pressure was released. Thus, if the jaws are partially closed, the jaws will remain in the partially closed position. In the bidirectional mode, the jaws can move in both directions in order to close or open. Thus, when the pressure on the lever 32 is released, the jaws open under influence of the return spring 80.

The unidirectional mode is chosen by moving the thumb lever 28 towards the distal end of handle 22. This causes wall member 114 to engage locking washer edge 118 and tip the locking washer 116 towards the distal end of the forceps 10. Lever 32 is depressed to actuate the jaws 34 and 36. As lever 32 pivots, it moves the inner tubular member 48 towards the distal end of forceps 10. This movement causes the sleeve support 144 to reach the arcuate portions 148 and 150 of the wire conductors 140 and 142 causing them to be drawn together thereby closing jaws 34 and 36 onto the tissue.

As the surgeon closes the jaws 34 and 36, he or she may intermittently stop applying pressure to the lever 32. The jaws will remain in their position when the surgeon stops applying pressure to the lever 32 because the frictional forces between the tipped washer 116 and the inner tubular member 48 prevent movement of the tubular member 48 in the rearward direction. The surgeon may then reapply pressure to lever 32 for closing the jaws 34 and 36 further. Each time the surgeon stops compressing the trigger 32, the jaws remain in the position where the finger pressure is relieved. This allows the surgeon to incrementally close the jaws and control the amount of compression applied to the tissue structures involved.

If the surgeon determines the jaws 34 and 36 have been closed too much, the lock release trigger 30 may be used to temporarily release the lock washer 116. The surgeon depresses the release trigger 30, thus causing the trigger to move the bottom portion 120 of the washer towards the distal end of the forceps 10. This causes the locking washer 116 to return to its perpendicular position relative to the inner tubular member 48. Because the inner tubular member 48 is no longer held in position with friction, it will move and open the jaws 34 and 36 by the return spring 80. When the lock release trigger 30 is released, the locking washer 116 resumes its tipped position.

In the event the surgeon wishes to have bidirectional movement, the locking thumb slide 28 is moved to its rearward position. Detent 110 is received in detent notch 106. In this position, the locking washer 116 is perpendicular to the inner tubular member 48. This allows the inner tubular member 48 to reciprocate back and forth without encountering any frictional forces from the edges of the locking washer 116 defining its aperture. The jaws 34 and 36 will close when pressure is applied to lever 32 causing the sleeve 144 to move over the arcuate portion 148 and 150 of the jaws 34 and 36. The jaws 34 and 36 will open when pressure on lever 32 is released.

When the surgeon has closed the jaws 34 and 36 on the tissue and is ready to cut and coagulate, RF power generated by an electrosurgical generator (not shown) is supplied, which causes a current path to be developed between the electrode surfaces 146 and 152 on the jaws to thereby heat and coagulate the tissue pinched between the jaw electrodes. The blade lever 24 of the handle 22 is then pivoted towards the distal end of handle 22. This causes the blade rod 50 to be longitudinally moved towards the distal end, causing the blade 26 to extend from the distal end 16 of the tubular member 12 between the conductor pairs and within the blade receiving slot. Once the tissue is cut, the blade 26 is retracted by removing pressure from the blade lever 22. The forceps jaws 34 and 36 may be released by temporarily releasing the locking mechanism through the trigger lever 30 or by moving the slide 28 to the unlocked or rearward position, depending upon whether the unidirectional or bidirectional mode has been selected.

This invention has been described here in considerable detail in order to comply with the patent statutes and to provide those skilled in the art with the information needed to apply the novel principles and to construct and use such specialized components as are disclosed. However, it is to be understood that the invention can be carried out by specifically different equipment and devices, and that various modifications, both to the equipment details and operating procedures, can be accomplished without departing from the scope of the invention itself.

What is claimed:

1. An electrosurgical device comprising:
    a) an elongated tubular member having a proximal end and a distal end;
    b) a pair of jaws at said distal end of said elongated tubular member moveable between an open position and a closed position;
    c) an actuating means operably connected to said proximal end of said elongated tubular member for actuating said pair of jaws between said open position and said closed position;
    d) a selector means operably connected to said actuating means for selecting movement of said pair of jaws between a unidirectional mode and a bidirectional mode; and
    e) a release means operably connected to said selector means for allowing bidirectional movement when said unidirectional mode is selected.

2. An electrosurgical device of claim 1 and further comprising a first electrode on a first jaw of said pair of jaws and a second electrode on a second jaw of said pair of jaws and means for applying a RF voltage across the first and second electrodes for coagulating tissue contained between said first and second jaws.

3. An electrosurgical device of claim 1 and further comprising a cutting instrument extending from said distal end of said elongated tubular member and reciprocating means for advancing and retracting said cutting instrument through tissue contained between said pair of jaws.

4. An electrosurgical device of claim 1 wherein said selector means comprises a reciprocally movable thumb slide member having a first position for selecting unidirectional mode and a second position for selecting bidirectional mode.

5. An electrosurgical device of claim 1 wherein said selector means includes a selective locking means for unidirectional movement of said pair of jaws from said open position to said closed position.

6. An electrosurgical device of claim 5 wherein said selective locking means has a first position frictionally engaging said tubular means when unidirectional mode is selected.

7. An electrosurgical device of claim 5 wherein said selective locking means has a second position not frictionally engaging said tubular means when bidirectional mode is selected.

8. An electrosurgical device of claim 5 wherein said selective locking means comprises a locking washer having an aperture through which said tubular means extends.

9. An electrosurgical device of claim 5 wherein said release means comprises a lever means for selectively engaging said locking means.

10. An electrosurgical device of claim 8 wherein said release means comprises a lever means for selectively engaging said washer to move said washer from frictionally engaging said tubular means.

11. An electrosurgical device of claim 1 wherein said actuating means includes an arcuate wire means extending proximal of said pair of jaws and further including a reciprocally longitudinally moveable tubular means for selectively engaging and deforming said arcuate wire means.

12. An electrosurgical device of claim 11 and further comprising means for imparting translational reciprocal motion to said actuating means including a trigger member operatively coupled to said moveable tubular means for imparting translational movement to said tubular means.

* * * * *